(12) United States Patent
Sereinig et al.

(10) Patent No.: US 8,853,434 B2
(45) Date of Patent: Oct. 7, 2014

(54) PROCESS FOR THE ISOMERISATION OF SUBSTITUTED ALKENES

(75) Inventors: Natascha Sereinig, Echt (NL); Michèle Catherine Christianne Janssen, Echt (NL); Johannes Gerardus De Vries, Echt (NL)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 14/129,201
(22) PCT Filed: Jul. 12, 2012
(86) PCT No.: PCT/EP2012/063679
§ 371 (c)(1), (2), (4) Date: Feb. 3, 2014
(87) PCT Pub. No.: WO2013/013990
PCT Pub. Date: Jan. 31, 2013

(65) Prior Publication Data
US 2014/0206898 A1    Jul. 24, 2014

Related U.S. Application Data

(60) Provisional application No. 61/510,562, filed on Jul. 22, 2011.

(30) Foreign Application Priority Data

Jul. 22, 2011  (EP) ..................... 11175033

(51) Int. Cl.
C11C 3/14    (2006.01)
C07C 67/333  (2006.01)
B01J 31/24   (2006.01)

(52) U.S. Cl.
CPC ............... *C07C 67/333* (2013.01); *B01J 31/24* (2013.01)
USPC ........................................................ 554/125

(58) Field of Classification Search
USPC ........................................................ 554/125
See application file for complete search history.

(56) References Cited

U.S. PATENT DOCUMENTS 2,847,432 A  *  8/1958  Steadman et al. ............ 562/524

FOREIGN PATENT DOCUMENTS

FR    1043797       11/1953
FR    1043797  A  *  11/1953

(Continued)

OTHER PUBLICATIONS

Fanjul et al: "Palladium complexes of the heterodiphosphine o-C6H4 (CH2PBu2)(CH2PPh2) are highly selective for the hydro", Organometallics., vol. 29, No. 10, Apr. 23, 2010, pp. 2292-2305.*
Fanjul et al., "Palladium Complexes of the Heterodiphosphine o-C6H4(CH2PtBu2)(CH2PPh2) Are Highly Selective and Robust Catalysts for the Hydromethoxycarbonylation of Ethene", Organometallics, vol. 29, pp. 2292-2305 (2010).

(Continued)

*Primary Examiner* — Deborah D Carr
(74) *Attorney, Agent, or Firm* — Miles & Stockbridge, PC

(57) ABSTRACT

The invention relates to a process for the isomerization of unsaturated fatty acids or esters or amides thereof, said process comprising reacting:
(a) an unsaturated fatty acid or ester or amide thereof;
(b) a source of Pd;
(c) a bidentate diphosphine of formula I,

R1R2>P1-R—P2<R3R4    (I)

wherein P1 and P2 represent phosphorus atoms; R1, R2, R3 and R4 represent tert-butyl; and wherein R represents an optionally substituted aromatic group spanning P1 and P2;
(d) a lower alcohol; and
(e) an acid co-catalyst,
under conditions for isomerization to take place.
The process is particularly advantageous for the isomerization of substituted alkenes harboring a hydroxy group when the desired end product has a keto group, such as ricinoleic acid or ester thereof.

8 Claims, 12 Drawing Sheets

Methyl oleate C18:1 (9)

Methyl linoleate C18:2 (9,12)

Methyl ricinoleate C18:1 (9), OH (12)

(56) References Cited

FOREIGN PATENT DOCUMENTS

| GB | 2148892 | | 6/1985 | |
| GB | 2148892 A | * | 6/1985 | ............. C07C 45/51 |
| WO | 90/12859 | | 11/1990 | |
| WO | WO 90/12859 | * | 11/1990 | |

OTHER PUBLICATIONS

International Search Report for PCT/EP2012/063679 Mailed May 10, 2012.

* cited by examiner

Methyl oleate

Methyl ricinoleate

PROCESS FOR THE ISOMERISATION OF SUBSTITUTED ALKENES

CROSS REFERENCE TO RELATED APPLICATIONS

This application is a §371 National Stage Application of PCT/EP2012/063679, filed Jul. 12, 2012, which claims priority to European Application No. 11175033.7, filed Jul. 22, 2011, and claims the benefit of U.S. Provisional Application No. 61/510,562, filed Jul. 22, 2011.

BACKGROUND OF THE INVENTION

1. Field of the Invention

The present invention relates to the isomerization of substituted alkenes.

2. Description of Related Art

The invention relates to a process for the isomerization of substituted alkenes such as unsaturated fatty acids or homoallyl-alcohols. Such a process is known from Colonge and Guyot, Bulletin de la Société Chimique de France, 1954, no. 69, p. 339-342. Colonge and Guyot describe the isomerization of the substituted alkene methylricinoleate (12-hydroxy-cis-9-octadecenoic acid methyl ester) to methyl-12-oxo-stearate using a Raney-Ni catalyst.

A problem of Raney-Ni catalysed isomerization reactions is that the temperature at which the reaction is carried out is relatively high, namely around 200° C. High temperatures are economically undesired for reasons of energy and equipment design, and also because the reaction selectivity usually decreases as the reaction temperature increases.

SUMMARY

It is an aim of the invention to provide a process for the isomerization of substituted alkenes which can be carried out at low temperatures.

It is another aim of the invention to provide a process for the isomerization of substituted alkenes which makes use of a soluble catalyst.

The invention provides a process for the isomerization of substituted alkenes comprising reacting:
(a) a substituted alkene;
(b) a source of Pd;
(c) a bidentate diphosphine of formula I, $$R1R2>P1-R-P2<R3R4 \quad (I)$$

wherein P1 and P2 represent phosphorus atoms; R1, R2, R3 and R4 independently represent the same or different optionally substituted organic groups containing a tertiary carbon atom through which the group is linked to the phosphorus atom and optionally comprising one or more heteroatoms; and wherein R represents a bridging group spanning P1 and P2 and comprising one or more carbon atoms and optionally one or more heteroatoms; and
(d) a reductant,
under conditions for isomerization to take place.

BRIEF DESCRIPTION OF THE DRAWINGS

FIGS. 1-12 represent embodiments as described herein.

DETAILED DESCRIPTION OF A PREFERRED EMBODIMENT

The term "a" or "an" as used herein is defined as "at least one" unless specified otherwise. When referring to a noun in the singular, the plural is meant to be included.

The inventors have found that the process is suitable for the isomerization of substituted alkenes.

The length of the bridge formed by R spanning P1 and P2 in the bidentate diphosphine of formula I may be between 1 and 20 atoms, more preferably between 2-10 atoms, even more preferably between 2 and 6 atoms.

The bidentate diphosphine of formula I may comprise R5-X-R6 wherein R5 and R6 independently represent optionally substituted alkylene groups and X represents an optionally substituted aromatic group.

R1, R2, R3, and R4 in the bidentate diphosphine of formula I may be tert-butyl, R3 and R4 may be methylene, and/or R may be ortho-phenylene. Alternatively, R1, R2, R3, and R4 may be tert-butyl, and/or R may be ortho-phenylene. A very suitable bidentate diphosphine of formula I is α,α'-bis(di-tert-butylphosphino)xylene. Other suitable R groups are ortho-naphthalene and ortho-anthracene The substitution of the alkene in the process may include hydroxyl or amine, and is preferably hydroxyl. The process may be particularly advantageous for substituted alkenes harbouring an hydroxyl group and where the desired end product is to have a keto group. Without wishing to speculate on the reaction mechanism, it appears that when a substituted alkene harbouring a hydroxylgroup is isomerized, the double bond of said substituted alkene may actually propagate across the alkene molecule toward the hydroxylgroup thereby forming an enol group, which may tautomerize into a keton.

The substituted alkene may be a homoallyl-alcohol.

The substituted alkene may be an unsaturated fatty acid or ester or amide thereof.

The notation with respect to the chemistry of fatty acids as used within the context of this invention is commonly used in the field of fat and oil chemistry. Fatty acids are named according to their lipid numbers. When taking C18:1 (9) as an example, the lipid number 18 indicates that the fatty acid chain consists of 18 carbon atoms (C18), the number 1 after the colon indicates that there is 1 double bond present in the chain, and the 9 between brackets indicates this double bond is at the 9' position of the chain. When referred herein to a carboxylic acid, e.g. stearic acid, such term is meant to include the protonated carboxylic acid (free acid), the corresponding carboxylate (its conjugated base), as well as a salt thereof, unless specified otherwise. Throughout this specification the use of "methyl oleate" and "oleic acid methyl ester", "methyl linoleate" and "linoleic acid methyl ester", "methyl ricinoleate" and "ricinoleic acid methyl ester", and "methyl-12-oxostearate" and "12-oxostearic acid methyl ester" shall have the same meaning.

Any unsaturated fatty acid may be isomerized. Suitable fatty acids are for example cis-9-hexadecenoic acid, cis-9-octadecenoic acid, cis,cis-9,12-octadecadienoic acid, cis,cis, cis-9,12,15-octadecatrienoic acid, cis,cis,cis,cis-6,9,12,15-octadecatetraenoic acid, cis,trans,trans-9,11,13 octadecatrienoic acid, 12-hydroxy-cis-9-octadecenoic acid, cis-9-eicosenoic acid, cis-11-eicosenoic acid, all cis-5,8,11, 14 eicosatetraenoic acid, all cis-8,11,14,17 eicosatetraenoic acid, all cis-5,8,11,14,17 eicosapentaenoic acid, cis-11-docosenoic, cis-13-docosenoic, all cis-7,10,13,16,19 docosapentaenoic acid, and all cis-4,7,10,13,16,19 docosahexaenoic acid.

A suitable unsaturated fatty acid is 12-hydroxy-cis-9-octadecenoic acid (ricinoleic acid) or its ester or amide, preferably its methylester. The process is particularly suitable for the isomerization of ricinoleic acid to 12-oxo-steareate, which is an industrially important molecule since it can be used to produce 12-aminostereate which is an intermediate in the production of polymers.

The unsaturated fatty acid may have more than one functionality, such as two hydroxyl groups, or three hydroxylgroups. A particularly suitable unsaturated fatty acid is a hydroxyl-substituted unsaturated fatty acid.

The unsaturated fatty acid may be in the form of a free fatty acid, its conjugated base, or salt, or a mixture thereof.

The unsaturated fatty acid may be an amide.

The unsaturated fatty acid may be an unsaturated fatty acid ester, i.e. the unsaturated fatty acid is esterified to a hydroxy-group-containing moiety. Said hydroxylgroup-containing moiety may contain one hydroxylgroup such as methanol or ethanol, two hydroxylgroups such as propylene glycol, three hydroxylgroups such as glycerol, or even more hydroxyl groups. Highly preferred are unsaturated fatty acid methyl esters.

The unsaturated fatty acid ester may be a glycerol ester, also referred to in the art as glyceride esters or glyceride oils. The term oil is generally used for fats that are liquid at normal room temperature, whereas the term fat is used to refer to fats that are solid at normal room temperature. Said glycerol ester includes mono-, di-, and triglycerides and mixtures thereof. When the glycerol ester is a monoglyceride it contains one unsaturated fatty acid. In the case of a diglyceride one or both of the fatty acids may be an unsaturated fatty acid. In the case of a triglyceride one, two, or three of the fatty acids may be an unsaturated fatty acid.

The unsaturated fatty acid ester may be an unsaturated fatty acid alkyl ester such as methyl, ethyl, or propyl ester. For reasons of cost a highly preferred unsaturated fatty acid ester is unsaturated fatty acid methyl ester.

The unsaturated fatty acid may be a functionalized unsaturated fatty acid. The functionality may include hydroxyl or amine, preferably hydroxyl. The unsaturated fatty acid may have more than one functionality, such as two hydroxyl groups, or three hydroxylgroups.

The unsaturated fatty acid may be ricinoleic acid.

The process may be carried out in the presence of carbonmonoxide. The inventors have found that the process can advantageously be carried out in the presence of carbonmonoxide mixed with one or more other gases, such as nitrogen. Preferably, the partial pressure of carbonmonoxide in the process is less than 20 bar, more preferably less than 10 bar, even more preferably less than 5 bar, even more preferably less than 3 bar, 2 bar, even more preferably less than 1 bar. Most preferably the amount of carbonmonoxide is approximately zero, e.g. below the detection limit. Ideally carbonmonoxide is absent in the reaction. The rate of isomerization in process is higher if the amount of carbonmonoxide is kept low.

Suitable sources of Pd in the process include its salts, such as for example the salts of palladium and halide acids, nitric acid, sulphuric acid or sulphonic acids; palladium complexes, e.g. with carbonmonoxide, dienes, such as dibenyzlideneacetone (dba) or acetylacetonate, palladium nanoparticles or palladium combined with a solid carrier material such as carbon, silica or an ion exchanger.

Preferably, a salt of palladium and a carboxylic acid is used, suitably a carboxylic acid with up to 12 carbon atoms, such as salts of acetic acid, proprionic acid, butanoic acid or 2-ethyl-hexanoic acid, or salts of substituted carboxylic acids such as trichloroacetic acid and trifluoroacetic acid. A very suitable source is palladium (II) acetate. The source of Pd may be selected from the group consisting of palladium halide, palladium carboxylate, and $Pd_2(dba)_3$.

The ratio of substituted alkene:Pd may be anywhere between 1:1 and 1,000,000, and is preferably between 1:100 and 1:50,000.

The process may done in the presence of a reductant. The reductant is not critical. The process of the invention may comprise (d) a lower alcohol. The lower alcohol may function as a reductant. The lower alcohol may be selected from C1, C2, C3, or C4 alcohols. Very suitable lower alcohols are methanol and ethanol. Suitable reductants are alkanols, preferably methanol. Other reductants are also suitable such as sodium borohydride. The ratio of reductant:Pd is preferably at least 1:1, preferably at least 10:1, more preferably at least 100:1, even more preferably at least 1000:1.

The process of the invention may be carried out in the presence of a solvent. The solvent may be the reductant, for example if the reductant is a lower alcohol such as methanol. The process may also be done in the presence of more than one solvent, for example in the presence of two or more alkanols selected from the group consisting of methanol, ethanol, isopropanol, and n-butanol. Other solvents may also advantageously be used depending on the solubility of the substituted alkene. Suitable solvents are DCM (dicholoromethane), DCE (dichloroethene), toluene, 2-ME-THF (2-methyl tetrahydrofuran), MTBE (methyl-ter-butylether), MiBK (methyl isobutylketone), HOAc (acetic acid), CPMe (cyclopentyl methylether), heptane, DMF (dimethyl formamide), NMP (N-methylpyrrolidone), THF (tetrahydrofuran), and DEGDME (diethyleneglycol dimethylether). Preferably, these solvents are used in combination with another alkanol, preferably with methanol. Nitrils are preferably avoided since they may be detrimental to the catalyst.

The process may further comprise (e) reacting with an acid co-catalyst, such as an acid having a pKa of 3 or less, preferably methanesulfonic acid. Reacting with an acid having a pKa of 3 or less may be advantageous when methanol is used as a reductant. Other suitable acid co-catalysts are Lewis acids and Brönsted acids.

The process is preferably done at a temperature of less than 210° C., more preferably less than 200° C., even more preferably less than 180° C., less than 160° C. Preferably the process is done at a temperature of between 25° C. and 150° C., more preferably between 30° C. and 130° C., even more preferably between 40° C. and 120° C., even more preferably between 50° C. and 100° C.

The invention further provides the use of a bidentate diphosphine of formula I, $$R1R2>P1-R-P2<R3R4 \quad (I)$$

wherein P1 and P2 represent phosphorus atoms; R1, R2, R3 and R4 represent tert-butyl; and wherein R represents an optionally substituted aromatic group spanning P1 and P2; for the isomerization of unsaturated fatty acids or esters or amides thereof.

Figure 1:
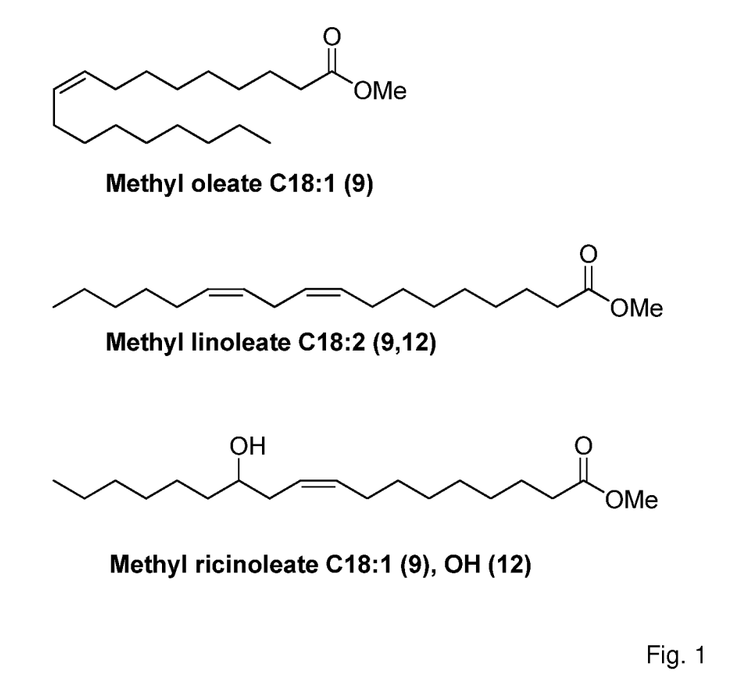

FIG. 1: Graphic representation of oleic acid methyl ester, linoleic acid methyl ester, and ricinoleic acid methyl ester.

Figure 2:
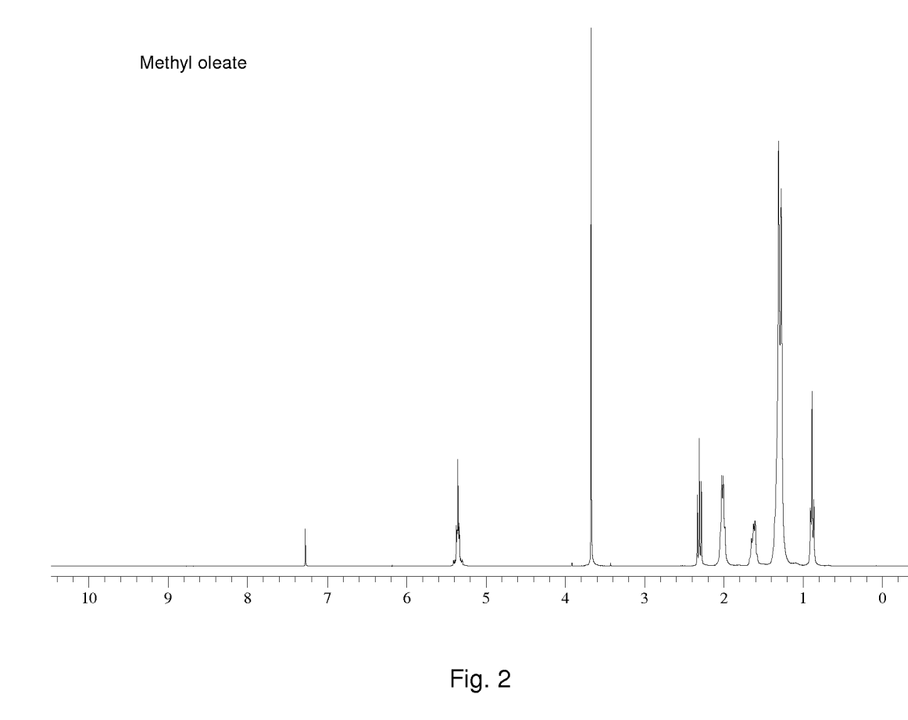

FIG. 2: NMR spectrum of oleic acid methyl ester before isomerization.

Figure 3:
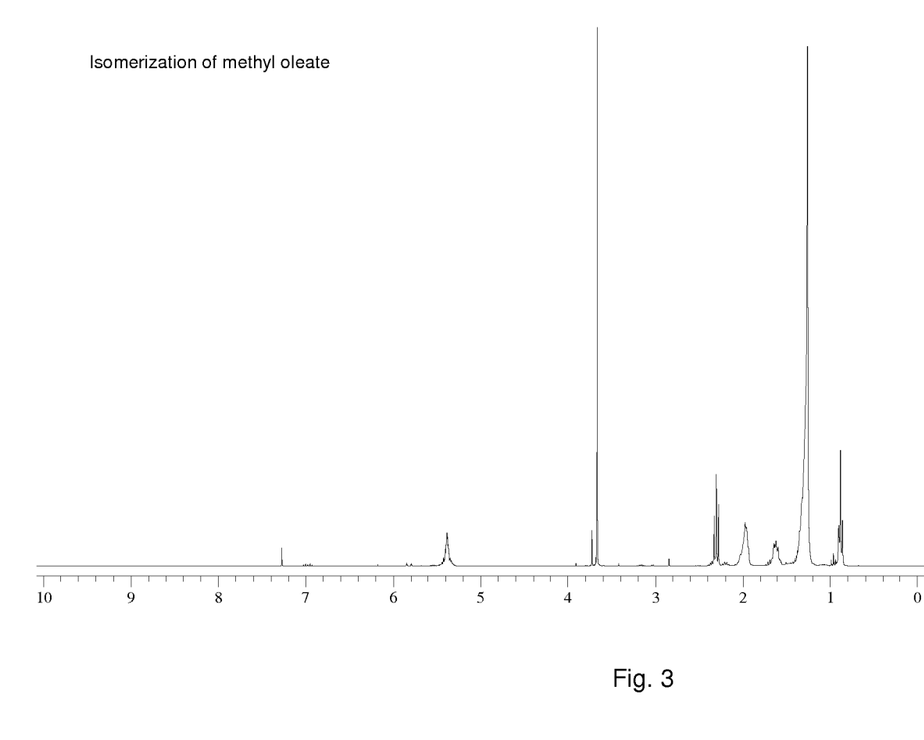

FIG. 3. NMR spectrum after isomerization of oleic acid methyl ester.

Figure 4:
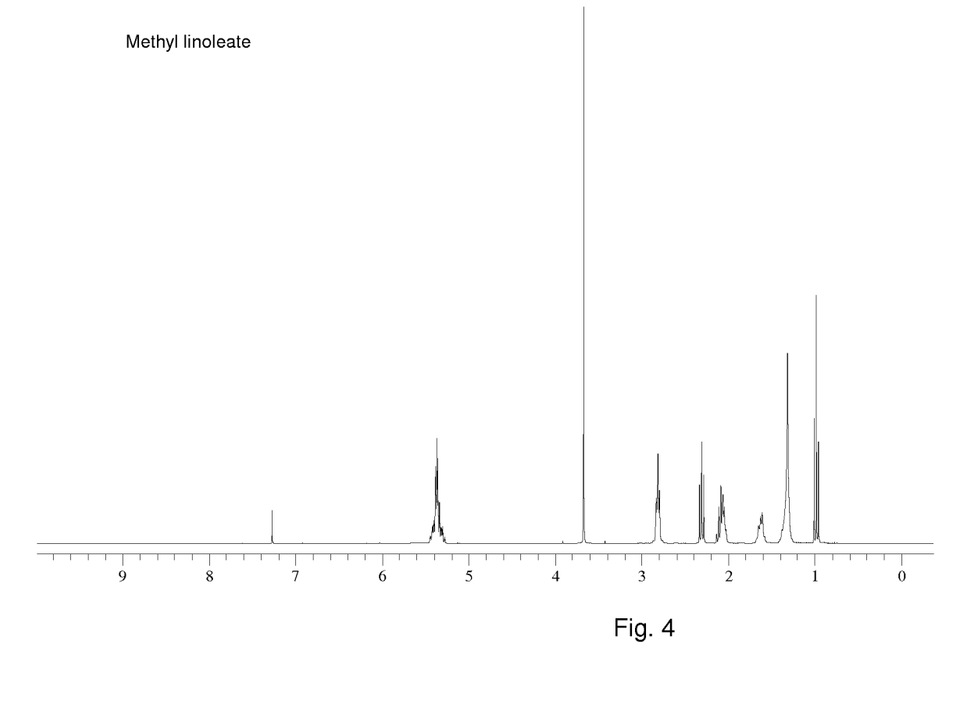

FIG. 4: NMR spectrum of linoleic acid methyl ester before isomerization.

Figure 5:
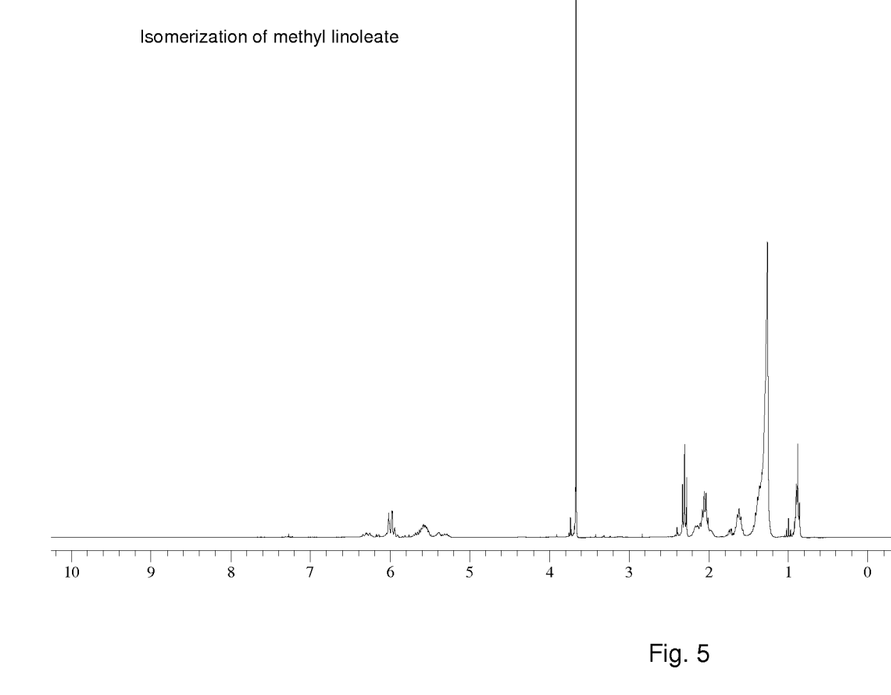

FIG. 5: NMR spectrum after isomerization of linoleic acid methyl ester.

Figure 6:
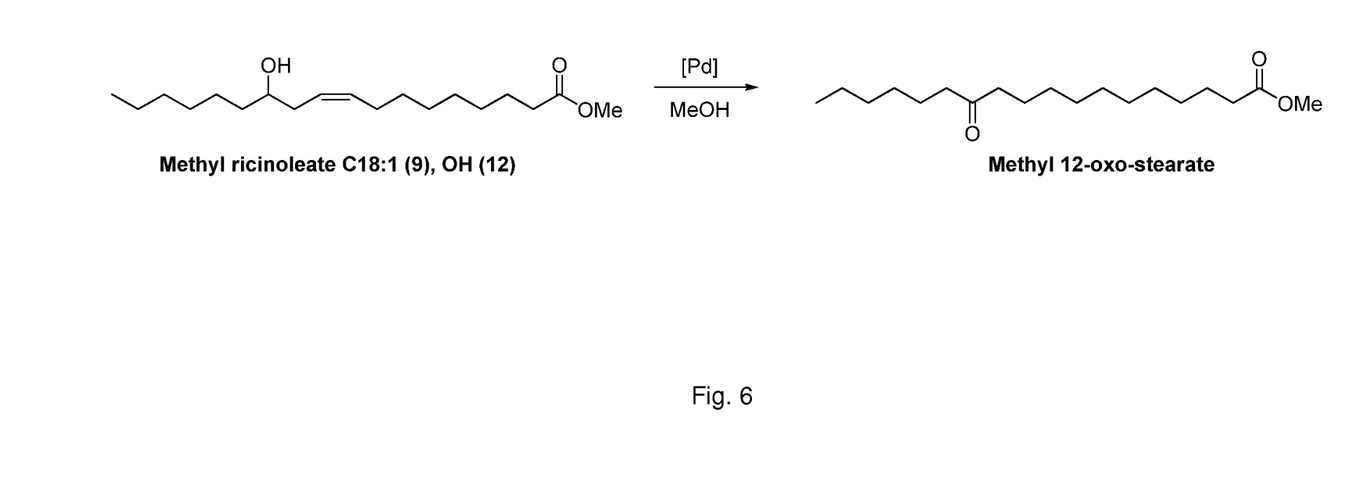

FIG. 6: Conversion of ricinoleic acid methyl ester to 12-oxostearate methyl ester.

Figure 7:
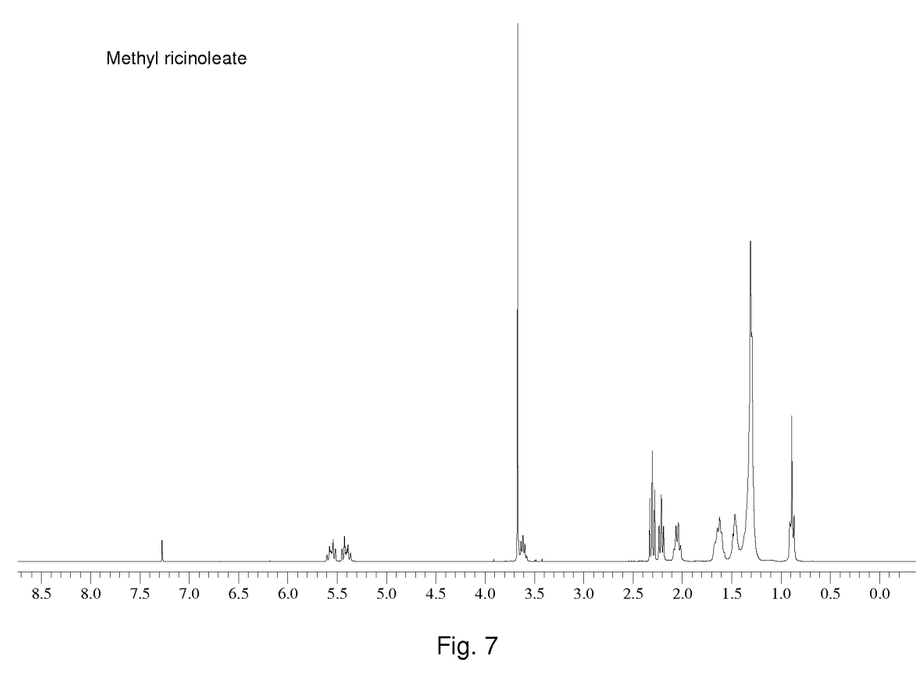

FIG. 7: NMR spectrum of ricinoleic acid methyl ester before isomerization.

Figure 8:
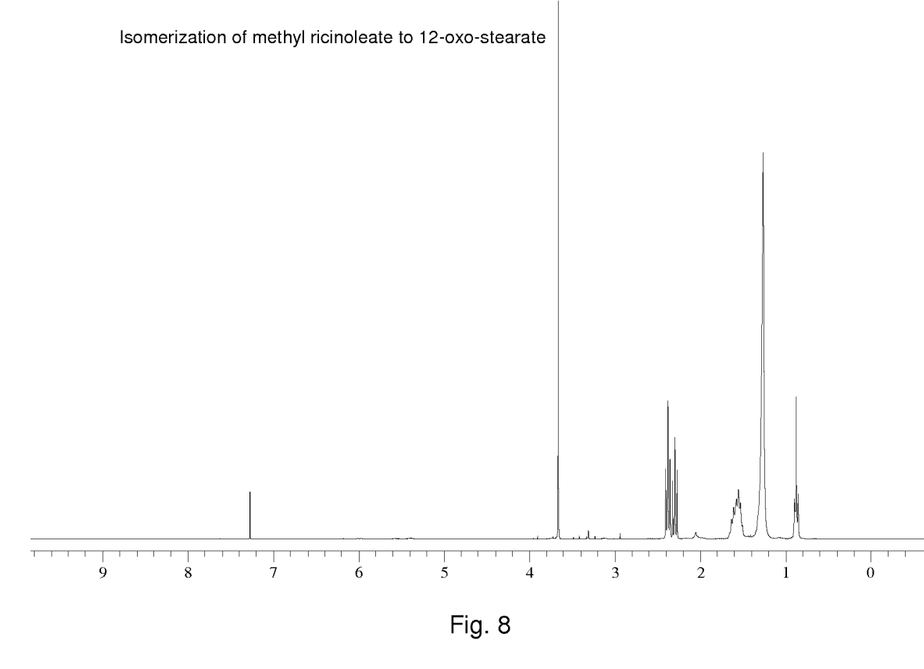

FIG. 8. NMR spectrum after isomerization of ricinoleic acid methyl ester.

Figure 9:
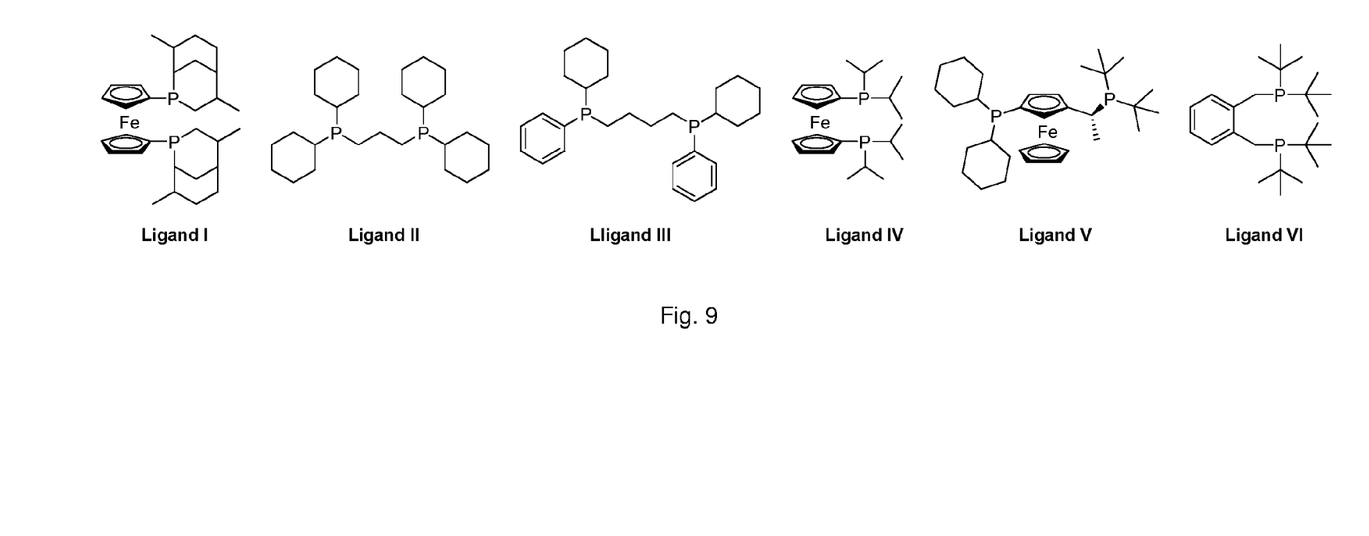

FIG. 9: Ligands I-VI used in isomerization experiments of ricinoleic acid methyl ester.

Figure 10:
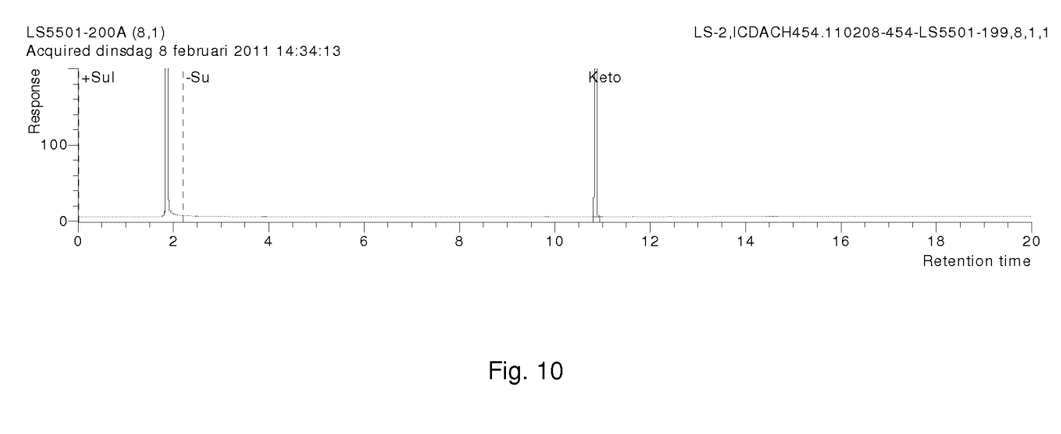

FIG. 10: GC analysis after isomerization of ricinoleic acid methyl ester with TBAB.

Figure 11:
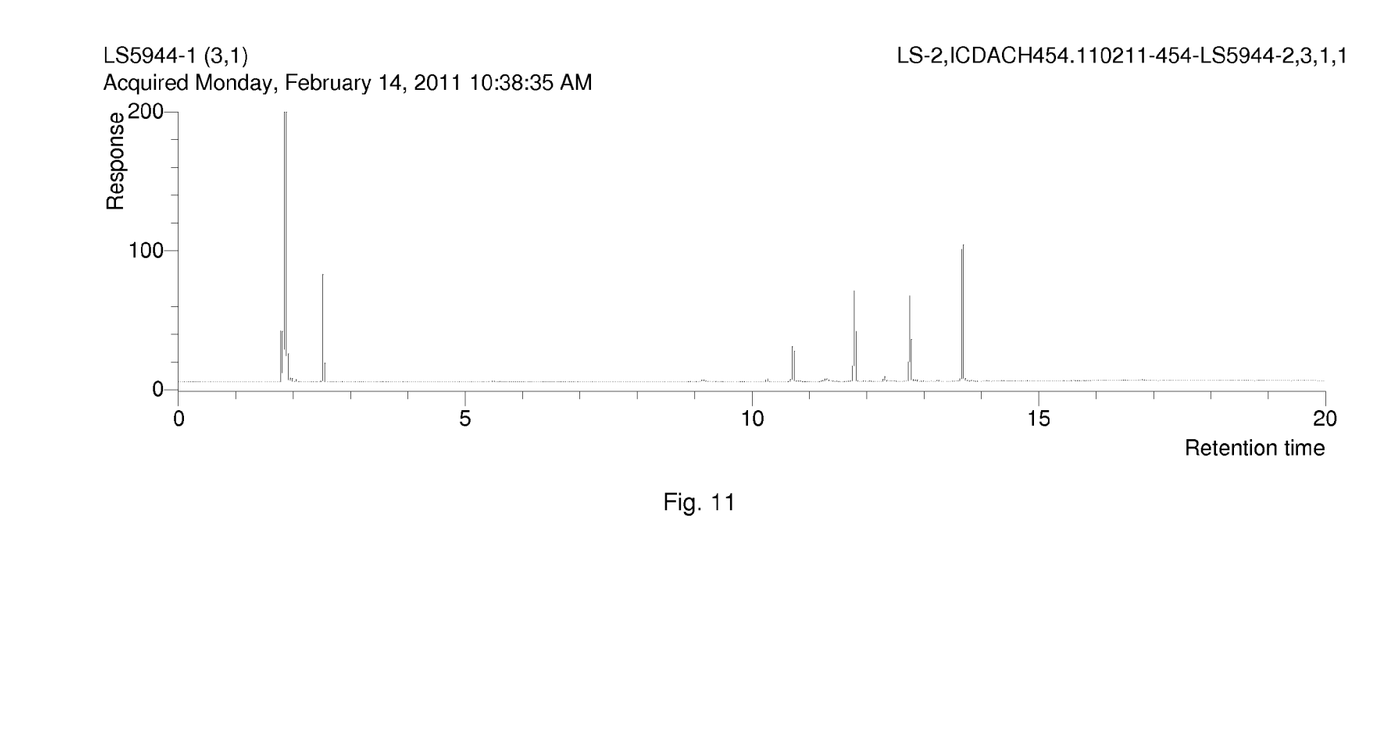

FIG. 11: GC analysis after isomerization of methyl ricinoleate in TBAB.

Figure 12:
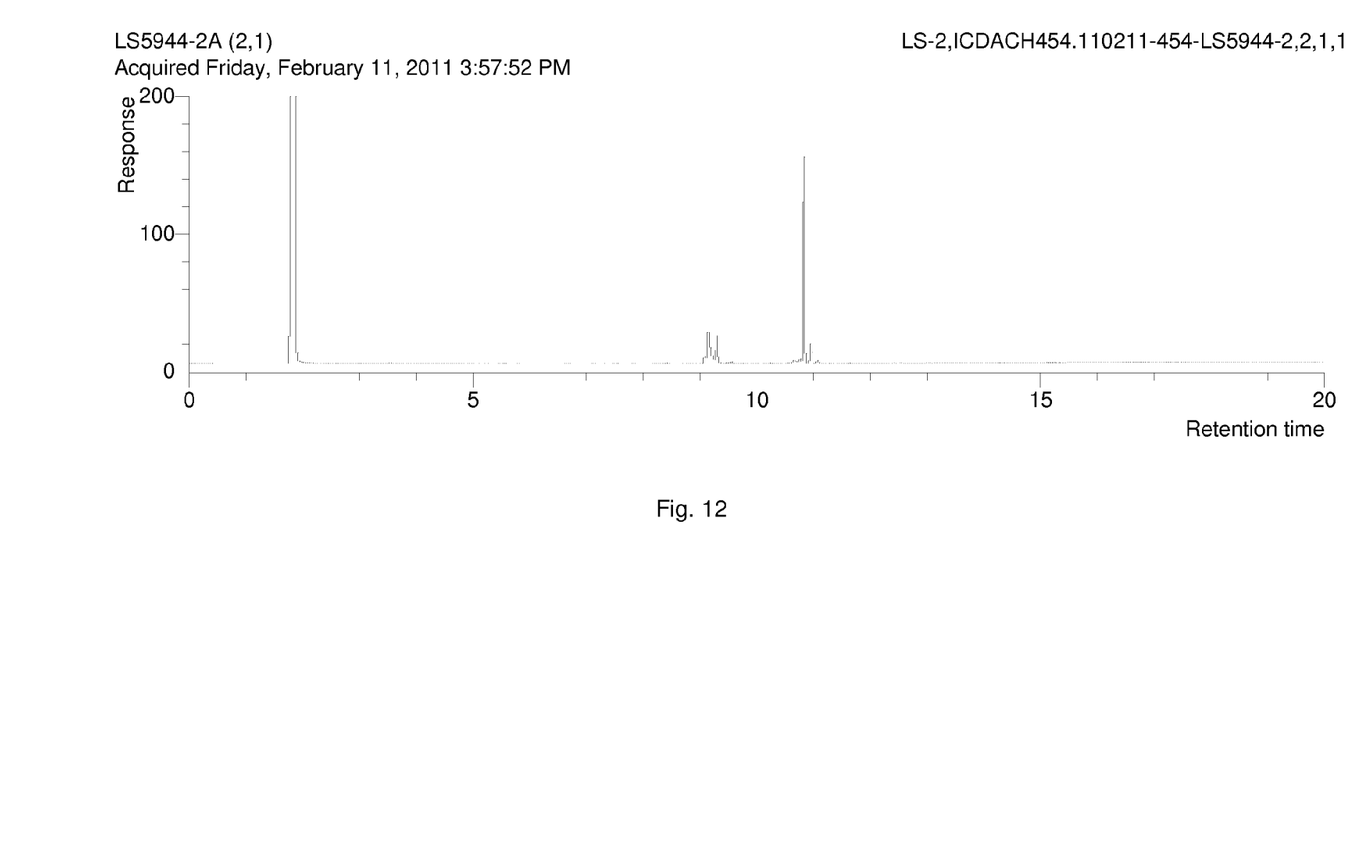

FIG. 12: GC analysis after isomerisation of methyl ricinoleate using Raney Ni.

The invention will be further elucidated with reference to the following examples, without however being limited thereto.

Example 1

Isomerization of Fatty Acid Methyl Esters

Pd(OAc)$_2$ (0.9 mg, 0.004 mmol) and α,α'-di-tert-butylphosphino-o-xylene (8 mg, 0.02 mmol) were dissolved in 5 mL of dry methanol. Subsequently, methanesulfonic acid (2.6 μL, 0.04 mmol) and 1 mmol of either oleic acid methyl ester (cis-9-octadecenoic acid methyl ester), linoleic acid methyl ester (cis,cis-9,12-octadecadienoic acid methyl ester) or ricinoleic acid methyl ester (12-hydroxy-cis-9-octadecenoic acid methyl ester) (FIG. 1) was added. The reaction was allowed to proceed for 4 h, and then the reaction mixtures were cooled down to room temperature (approximately 23° C.) and analyzed by means of NMR. The results are summarized in Tables 1-3.

From the NMR spectra it is apparent that both methyl oleate and methyl linoleate are isomerized in the presence of a Pd-catalyst in methanol to a statistic mixture of isomers (FIGS. 2-5). After isomerization of oleic acid methyl ester, 95% is a mixture of different isomers each having a double bond at a position which can range between C atom 3 to C atom 17; the actual position of the double bond cannot be easily distinguished from the NMR spectra. However it is possible from the NMR spectrum to identify isomers having a double bond at the 2 position. When the double bond is at the 2 position it is conjugated with the carboxylic acid group; 6% respectively 5% of the double bond in the isomerization product of oleic acid methyl ester is conjugated after reaction at 50° C. and 100° C. respectively. In methyl oleate after isomerization the double bond can in theory occur at 16 different positions (C2-C17), so if there was no preference each position would have approximately 1/16=6% likelihood. Therefore when 5 to 6% of the double bond is conjugated with the carboxylic acid this indicates that isomerization was very efficient.

In Table 2, the "x" in (2,x) (last column) means that the second double bond (the first double bond being at the 2 position) may be anywhere between C4 and C17; the actual position of the second double bond can not easily be identified from the NMR spectrum.

After isomerization of linoleic acid methyl ester (which has two double bonds) at 50° C., 57% of the reaction product consists of a mixture of different isomers having a double bond at a position which is anywhere between the C atom 3 through 17, whilst the percentage of the linoleic acid isomerization product which has a double bond which is conjugated, is 43% respectively 96% after reaction at 50° C. and 100° C., respectively.

Interestingly, 37% respectively 100% of the isomerization reaction product of ricinoleic acid methyl ester after reaction at 50° C. and 100° C., respectively, was shown to be methyl-12-oxo-stearate. This indicates that during the reaction the hydroxylgroup of the molecule is converted to a keto functionality (Table 3 and FIGS. 6-8).

TABLE 1

Isomerization of oleic acid methyl ester

| Entry | Lipid number | T (° C.) | C18:1 (%) | C18:1 (2) (%) |
|---|---|---|---|---|
| 1 | C18:1 (9) | 50 | 95 | 6 |
| 2 | C18:1 (9) | 100 | 95 | 5 |

TABLE 2

Isomerization of linoleic acid methyl ester

| Entry | Lipid number | T (° C.) | C18:2 (%) | C18:2 (conjugated) (%) | C18:2 (2, x) (%) |
|---|---|---|---|---|---|
| 3 | C18:2 (9, 12) | 50 | 57 | 43 | |
| 4 | C18:2 (9, 12) | 100 | | 96 | 4 |

TABLE 3

Isomerization of ricinoleic acid methyl ester

| Entry | Lipid number | T (° C.) | C18:1, OH (%) | C18:1(2), OH (%) | Keto (%) |
|---|---|---|---|---|---|
| 5 | C18:1 (9), OH (12) | 50 | 58 | 5 | 37 |
| 6 | C18:1 (9), OH (12) | 100 | | | 100 |

Example 2

Isomerization of Ricinoleate Using Different Ligands

Pd(OAc)$_2$ (0.45 mg, 0.002 mmol) and one of Ligands I through VI (FIG. 9) (0.01 mmol) were dissolved in 5 mL of dry methanol. Subsequently, methanesulfonic acid (1.3 μL, 0.02 mmol) and ricinoleic acid methyl ester (1 mmol, 338 μL) were added. The reaction was allowed to proceed at 100° C. for 4 h, and then the reaction mixtures were cooled down to room temperature and analyzed by means of GC.

TABLE 4

Isomerization of ricinoleate

| Entry | Ligand | Methyl ricinoleate (area %) | Methyl-12-oxo-stearate (area %) |
|---|---|---|---|
| 7 (comparative example) | I | 68 | 17 |
| 8 (comparative example) | II | 69 | 17 |
| 9 (comparative example) | III | 89 | 4 |
| 10 (comparative example) | IV | 88 | 4 |
| 11 (comparative example) | V | 79 | 4 |
| 12 | VI | 0 | 77 |

Example 3

Isomerization of Methyl Ricinoleate

Pd(OAc)$_2$ (6.6 mg, 0.03 mmol) and α,α'-di-tert-butylphosphino-o-xylene (59 mg, 0.15 mmol) were dissolved in 30 mL of dry methanol. Subsequently, methanesulfonic acid (20 μL, 0.3 mmol) and ricinoleate (5 mL, 15 mmol). The reaction was allowed to proceed at 100° C. for 4 h, and then the reaction mixtures were cooled down to room temperature and the crystals were filtered off and washed with methanol. The products were analyzed with GC (FIG. 10). The weight of the product was 4.63 g which corresponds to a yield of 93%. The reaction selectivity was 100%.

In a second experiment, Pd(OAc)$_2$ (6.5 mg, 0.029 mmol) and α,α'-di-tert-butylphosphino-o-xylene (59 mg, 0.15 mmol) were dissolved in 30 mL of dry methanol. Subsequently, methanesulfonic acid (20 μL, 0.3 mmol) and ricinoleate (290 mmol). The reaction was allowed to proceed at reflux (i.e. at a temperature of around 65° C.) for 24 h (conv. 80%), and then an identical amount of freshly prepared catalyst was added to the reaction mixture. After another 24 h of reflux, the reaction had reached completion and the mixture was allowed to cool down to room temperature and the crystals were filtered off and washed with methanol. The reaction mixture was analyzed with GC and showed only methyl-12-oxo-stearate.

Comparative Example A

Isomerization of Methyl Ricinoleate in TBAB 1.52 g Aliquat 100 (tetrabutyl ammonium bromide, TBAB) and 8.3 mg Pd(OAc)$_2$ were placed in a 5 mL vial with crimp cap. This mixture was heated to 120° C. under vacuum for 2.5 hours. The vial was put under N$_2$-atmosphere and 312 mg (1 mmol) methyl ricinoleate was added. This mixture was heated to 120° C. for 94 hours. The product was extracted from the TBAB with heptane. After concentration 172 mg was obtained. The reaction products were analyzed by GC (FIG. 11): 8 area % methyl ricinoleic acid methyl ester, 15 area % at 2.54', 21 area % at 11.8', 20 area % at 12.77' and 33 area % at 13.69'. No 12-oxostearate methyl ester was formed.

Comparative Example B

Isomerisation of Methyl Ricinoleate Using Raney Ni

In a 25 mL pointed bottom flask 1.3 g Raney Ni was washed with MeOH, 3.54 g of ricinoleic acid methyl ester was added and the mixture was heated to 210° C. for 3 hours. After cooling the mixture was diluted with MeOH. The catalyst was filtered off, and the filtrate was concentrated by evaporation under vacuum. Yield: 3.28 g. The reaction products were analyzed by GC (FIG. 12) which showed the production of 61 area % methyl-12-oxostearate and no detectable amounts of ricinoleic acid methyl ester. The reaction selectivity was 61%.

Example 4

Solvents for the Isomerization of Ricinoleic Acid Methyl Ester

Pd(OAc)$_2$ (0.45 mg, 0.002 mmol) and α,α'-di-tert-butylphosphino-o-xylene (4 mg, 0.01 mmol) were dissolved in 4 mL of either one of the solvents of Table 5. Subsequently, methanesulfonic acid (1.3 μL, 0.02 mmol) and ricinoleate (1 mmol, 338 μL) were added. The reaction was allowed to proceed at the temperature and time as indicated in Table 5. The reaction mixtures were cooled down to room temperature and analyzed by means of GC. The results are summarized in Table 5.

TABLE 5

Solvents for the isomerization of of ricinoleic acid methyl ester

| Entry | Solvent | T (° C.) | Time (h) | Ricinoleic acid methyl ester (area %) | methyl-12-oxo-stearate (area %) |
|---|---|---|---|---|---|
| 13 | MeOH | 85 | 4 | 0 | 76 |
| 14 | EtOH | 85 | 8 | 0 | 25 |
| 15 | iPrOH | 85 | 4 | 56 | 4 |
| 16 | n-BuOH | 85 | 8 | 0 | 16 |
| 17 | MeCN | 85 | 4 | 90 | 0 |
| 18 | DCM | 40 | 17 | 98 | 0 |
| 19 | DCE | 85 | 4 | 99 | 0 |
| 20 | Toluene | 85 | 4 | 99 | 0 |
| 21 | 2-Me—THF | 85 | 4 | 98 | 0 |
| 22 | MTBE | 40 | 17 | 98 | 0 |
| 23 | MiBK | 85 | 4 | 99 | 0 |
| 24 | HOAc | 85 | 4 | 76 | 0 |
| 25 | CPMe (1) | 85 | 4 | 99 | 0 |
| 26 | Heptane | 85 | 4 | 99 | 0 |
| 27 | DMF | 85 | 4 | 60 | 5 |
| 28 | NMP | 85 | 4 | 94 | 0 |
| 29 | THF | 40 | 17 | 97 | 0 |
| 30 | DEGDME (2) | 85 | 4 | 94 | 0 |

(1) cyclopentyl methylether;
(2) diethyleneglycol dimethylether

The invention claimed is:

1. A process for the isomerization of unsaturated fatty acids and/or an ester and/or an amide thereof, said process comprising reacting:
    (a) an unsaturated fatty acid and/or ester and/or amide thereof;
    (b) a source of Pd;
    (c) a bidentate diphosphine of formula I,

R1R2>P1-R—P2<R3R4     (I)

wherein P1 and P2 represent phosphorus atoms; R1, R2, R3 and R4 represent tert-butyl; and wherein R represents an optionally substituted aromatic group spanning P1 and P2;
    (d) a lower alcohol; and
    (e) an acid co-catalyst,
    under conditions for isomerization to take place.
2. The process according to claim 1, wherein R is ortho-phenylene, ortho-naphthalene, or ortho-anthracene.
3. The process according to claim 1, wherein the bidentate diphosphine is α,α'-bis(di-tert-butylphosphino)xylene.
4. The process according to claim 1, wherein the unsaturated fatty acid is a hydroxyl-substituted unsaturated fatty acid.
5. The process according to claim 1, wherein the unsaturated fatty acid is ricinoleic acid and/or ester thereof.
6. The process according to claim 1, wherein the process is carried out in the presence of carbonmonoxide which is present at a partial pressure of not more than 20 bar.
7. The process according to claim 1, wherein the process is carried out at a temperature of from 25° C. to 150° C.
8. A bidentate diphosphine of formula I,

R1R2>P1-R—P2<R3R4     (I)

wherein P1 and P2 represent phosphorus atoms; R1, R2, R3 and R4 represent tert-butyl; and wherein R represents an optionally substituted aromatic group spanning P1 and P2;
    capable of being used for isomerization of an unsaturated fatty acid and/or an ester and/or an amide thereof.

* * * * *